United States Patent [19]

Janssen et al.

[11] Patent Number: 4,723,261
[45] Date of Patent: Feb. 2, 1988

[54] X-RAY EXAMINATION APPARATUS INCORPORATING IMAGE SUBTRACTION

[75] Inventors: Jozef T. A. Janssen; Adrianus C. van Benthem, both Eindhoven, Netherlands

[73] Assignee: U.S. Philips Corporation, New York, N.Y.

[21] Appl. No.: 685,649

[22] Filed: Dec. 24, 1984

[30] Foreign Application Priority Data

Dec. 22, 1983 [NL] Netherlands ............... 8304397

[51] Int. Cl.$^4$ ............................... H05G 1/64
[52] U.S. Cl. ........................ 378/99; 358/111; 128/654
[58] Field of Search ............ 378/99, 4; 358/111; 128/654

[56] References Cited

U.S. PATENT DOCUMENTS

| | | | |
|---|---|---|---|
| 4,448,200 | 5/1984 | Brooks et al. | 358/111 |
| 4,477,923 | 10/1984 | Baumann et al. | 378/99 |
| 4,514,759 | 4/1985 | Amtmann | 358/111 |
| 4,543,604 | 9/1985 | Grosse | 358/111 |
| 4,551,800 | 11/1985 | Riederer et al. | 358/111 |
| 4,581,635 | 4/1986 | Franke | 378/99 |
| 4,613,983 | 9/1986 | Yedid et al. | 378/99 |
| 4,626,908 | 12/1986 | Tani | 378/99 |

FOREIGN PATENT DOCUMENTS 0101746 3/1984 European Pat. Off. ............... 378/4

*Primary Examiner*—Craig E. Church
*Assistant Examiner*—John C. Freeman
*Attorney, Agent, or Firm*—Jack E. Haken

[57] ABSTRACT

An X-ray examination apparatus incorporating digital image subtraction in which from a series of images to be formed of an object with and without contrast medium those images are selected for subtraction which result in ultimate images which combine a low motional unsharpness with adequate contrast. Images are also formed on at least one of the edges of the contrast bolus, so that in each position several contrast images can be formed with a single contrast bolus.

3 Claims, 2 Drawing Figures

X-RAY EXAMINATION APPARATUS INCORPORATING IMAGE SUBTRACTION

The invention relates to an X-ray examination apparatus comprising an X-ray source, an X-ray image detection device, a television camera device, and a device for digital image subtraction which comprises an analog-to-digital converter, a readable digital image memory, and an image display device, and also relates to a method of performing X-ray examinations by means of such an apparatus.

An X-ray examination apparatus of this kind is known from U.S. Pat. No. 4,204,225. In a device for digital vascular imaging (DVI) which is disclosed therein, X-ray images are recorded without a contrast medium and with a contrast medium, respectively, said images being subtracted after digitizing so that, in principle, an image of the local distribution of the contrast medium and hence of, for example the vascular system is formed. During examination of, for example parts of the body which do not fit within a single image field of the X-ray image intensifier tube, problems are encountered because images must then be formed in a plurality of positions. In the case of venous injection the amount of contrast medium required for suitable imaging in the various positions may become objectionably large and often problems are experienced as regards the linking of the various areas in order to form a total image. For angiographic examinations notably the part of the human body which comprises the bifurcation of the vascular system and at least a part of the legs is important.

It is the object of the invention to enable digital substraction examinations also for larger parts of the body; to this end, an X-ray examination apparatus of the kind set forth in accordance with the invention is characterized in that for the examination of objects having a lateral dimension which is larger than the entrance screen of the X-ray image detection device is provided a movement mechanism for a mutual lateral displacement of the X-ray source and the X-ray image detection device on the one side and the object on the other side in a manner which is correlated with the propagation of a contrast medium flowing through the object to be examined.

Because in a device in accordance with the invention the imaging field is displaced, for example at the speed of movement of the bolus of a contrast medium, the contrast medium introduced by a single injection can be used for several exposures. Moreover, a selection can be made from various methods as regards the sequence of formation of images without contrast medium (to be referred to hereinafter, as mask images) and images with contrast medium (referred to hereinafter as contrast images). For example, first a series of mask images can be taken across the entire the part of the body to be examined, after which a contrast medium is administered and a series of contrast images are formed as the contrast medium progresses, in the positions corresponding to the mask images. The imaging mechanism can then be moved in discrete steps as well as continuously. It is a drawback of this method that a large period of time expires between the mask image and the contrast image, so that unsharpness may occur due to motions of or in the patient.

This drawback is mitigated in a preferred embodiment of the invention in that the mask images and the contrast images are formed in a single series, that is to say so that in each position on an edge of the contrast bolus a mask image is formed with a comparatively low contrast medium concentration and an contrast image is formed with a comparatively high concentration. In the case of a mask image made at the trailing end of the bolus and an image made nearer to the apex thereof, almost the entire contrast medium of the bolus can still be used. It may be a drawback that the time interval between mask image and image, now dictated entirely by the flow rate of the bolus, may not be optimum for a given examination or a given region, so that in practice it is still too long and the bolus has proceeded too far to a next position after the recording of the image. This drawback can be mitigated by forming the mask image and the image in a comparatively rapid succession on the steepest part of the edge of the bolus, for example on both sides of the standard deviation thereof. When the images are taken approximately 0.5 seconds apart, approximately one quarter of the maximum concentration of contrast medium will be effectively used, which is amply sufficient for making a series of images wherefrom an optimum image can be selected at a later stage. It is an additional advantage that both images can be formed also at the trailing end of the bolus. When used is made of the latter methods, repositioning will not be necessary, at least not for the mask images, because they are all formed in a single series. Because the images to be subtracted from one another are taken in a direct or an at least substantially direct succession, motional unsharpness will be avoided.

A preferred embodiment utilizes a 14" X-ray image intensifier tube as described in U.S. Pat. No. 4,213,055 for the X-ray image detection device. Consequently, not only a large image field is obtained but measurements can also be performed with less contrast medium due to the favourable imaging qualities thereof. A detection system for automatic exposure control may be included in the television chain or in the light transmission between the X-ray image intensifier tube and the television camera tube of the image intensifier/television chain.

An extremely suitable X-ray imaging apparatus for carrying out the invention wherein the system formed by the X-ray tube and the image intensifier system can be displaced in rapid succession in very precise steps or continuously with respect to a patient is described in British patent document No. 2098440. If desired, several mask images and several contrast images can be formed in any position, so that the quality of the ultimate image can be optimized for diagnostice purpose. In order to prevent the occurrence of overradiation in the image due to radiation which reaches the entrance screen of the X-ray image intensifier tube without having passed through the object material, a further preferred embodiment utilizes a radiation filter as disclosed in U.S. patent application Ser. No. 677,938. The filter has a radiation absorption which varies in a longitudinal direction as well as in a transverse direction, so that overradiation through the space between the legs is prevented.

Some preferred embodiments in accordance with the invention will be described in detail hereinafter with reference to the accompanying drawing. Therein:

Figure 1:
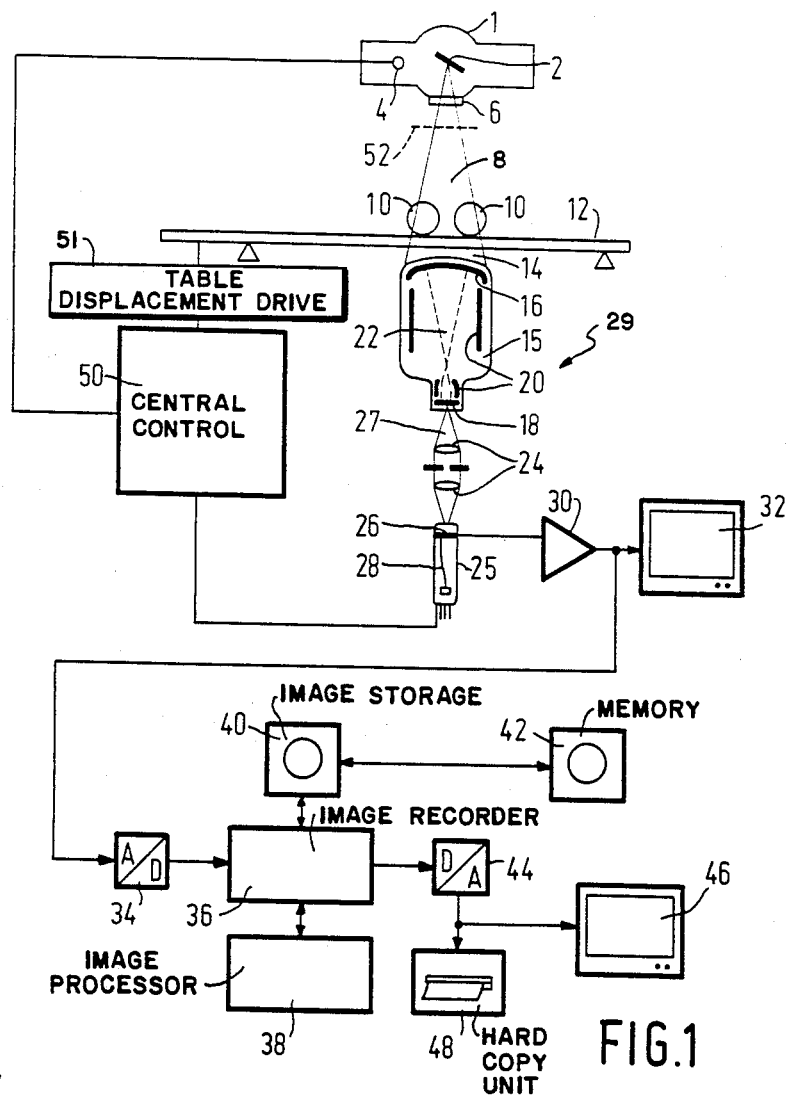
FIG. 1 shows an X-ray examination apparatus in accordance with the invention.

An X-ray examination apparatus as shown in FIG. 1 comprises an X-ray tube 1, having an anode 2, cathode 4 and an exit window 6, for generating an X-ray beam 8 whereby an object 10 which is situated on an object table 12 can be irradiated. At the side of the object table which is remote from the X-ray source an X-ray image intensifier tube 15 is arranged in the X-ray beam 14 which now carries image information, said intensifier tube comprising an entrance screen 16, an exit screen 18 and an electron-optical system 20 for imaging an electron beam 22, released from a photocathode of the entrance screen by the X-ray beam 14, onto the exit screen. The exit screen 18 is optically coupled to an entrance screen 26 of a television camera tube 25 by means of either a fibre-optical system, or, as in the present case, by means of a lens system 24. An image which is projected onto the entrance screen 26 of the television camera tube by a light beam 27 is scanned by means of an electron beam 28 in order to be converted into a video signal. The X-ray tube, together with a detection system 29 and the object carrier 12 form parts of the X-ray examination apparatus disclosed in British Patent 2,098,440 in which the X-ray source 1 with the detection system 29 can be displaced with respect to the object carrier in the discribed manner, The video signal is applied, via a pre-amplifier 30, to a first monitor 32 and to an analog-to-digital converter 34 in which analog video signals are converted into digitized image signals which can be applied for further processing to a digital image recording device 36 which comprises a digital image processing unit 38 and a first image storage device 40, for example a magnetic disc, and a second memory 42, for example a digital optical memory in which image information can be stored for a prolonged period of time in an addressable manner. A resultant digital image can be displayed from the memory unit, via a digital-to-analog converter 44, on a television monitor 46 or be recorded as a hard copy via a hard copy unit 48. A central control unit 50 is provided for control and, wherever necessary, synchronization of the television camera tube, the X-ray tube and the position of the object table by a table displacement drive 51 and hence of the object.

With the central control unit 50 there may be associated an EEG recording and trigger unit whereby on the one hand an EEG of a patient to be examined can be recorded whilst on the other hand, possible correlated there with, the optimum instant for administering an injection contrast medium can be indicated.

The X-ray image intensifier tube 15 is preferably formed by a 14" high-resolution tube as described in U.S. Pat. No. 4,213,055. Using such a tube, a diagnostically important, consecutive area of a patient to be examined can be covered from the bifurcation as far as the feet with a diagnostically adequate image overlap in, for example 8 consecutive positions. To this end, after positioning and conditioning of the patient, a consecutive series of mask images can be formed, after which a contrast medium is administered and a corresponding series of images is made while following the contrast bolus. Notably during the formation of the images a plurality of exposures can be made in each position, after which each time the radiation detection system is advanced one position. However, displacement can alternatively be continuously performed, at a constant speed or not. The central control unit then activates the X-ray tube in a pulsed manner in positions defined by the position of the object carrier during the formation of the mask images. It is an advantage of continuous displacement that there will be no apparatus shocks. The continuous method of displacement can also be used for the embodiments to be described hereinafter, with the exception of the stepped time interval difference (TID) method. Each of the images formed can be displayed directly on a monitor and be checked for the degree of contrast produced therein by the contrast medium, so that the movement can be adapted. The further formation of local difference images from mask images and contrast images is performed by using conventional techniques. The difference images can also be displayed on-line on a monitor, or stored, for example in a "DOR" (Digital Optical Recording) system for later analysis, or be recorded as a hard copy.

It is a major drawback of this method of measuring that the period of time expiring between the formation of the mask image and the contrast image cannot be substantially less than from 10 to 20 seconds. Motions of the patient often disturb the imaging. In this respect it is irrelevant whether the displacement is performed continuously or intermittently. In the case of continuous displacement, spring-like motions inside the patients are avoided when patient himself is displaced. It will be apparent that the repositioning of the patient must also be extremely precise when these methods are used, because any misalignment between mask image and contrast image essentially occurs also as a motional artefact in the difference image.

A substantial improvement can be achieved in respect of image distortion by patient motions by using a stepped TID method of measurement. According to this method, the measurements are performed so that in each position a mask image is formed as well as a contrast image, without any intermediate displacements. Even though the terms mask image and contrast image are used for the sake of simplicity in this respect, several mask images and notably several contrast images may also be formed in each position. After positioning and conditioning of the patient, for example a controlled injection with contrast medium is performed, followed by the formation of a mask exposure as soon as the medium flows into the measurement field, and a contrast image when the contrast medium has penetrated the measurement filed to a given extent. Subsequently, the imaging system is displaced over one step and corresponding measurements are performed in a second position. Because several images are formed in each position, in this case continuous displacement is not relevant as has already been stated. Storage, display, processing and recording of the image information is again performed in known manner.

It is a problem that the displacement to a next position can be performed when the last mask image has been formed. Consequently, the contrast medium may not have penetrated too far into measurement field of the next position. Considering this condition, the flow rate of the contrast medium as well as the length of the bolus in the patient are relevant. This problem can be solved by injecting fresh contrast medium for each position. However, it is a drawback that, like for normal DVI examinations of such a large region, the amount of contrast medium exceeds the upper limit imposed. For regions which are not excessively large, the 14" X-ray image intensifier tube can be used for performing this method.

Figure 2:
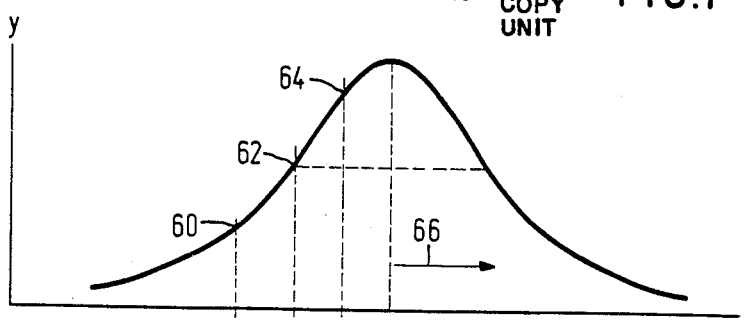
FIG. 2 shows an example of a contrast bolus in which optimum exposure positions are indicated.

In order to mitigate the drawbacks of the large dose of contrast medium, a preferred version of the method in accordance with the invention involves the formation of a mask image as well as a contrast image in each successive position with one and the same contrast medium bolus. For the mask image, however, a position is chosen with respect to the contrast bolus on a side of an edge portion of the bolus where the variation in the concentration is comparatively large instead of a position in which the concentration is still very low. An attractive position is denoted by the reference mumeral 60 in FIG. 2, that is to say, measured in the concentration plotted in the Y-direction, approximately from 10 to 20% before the reversing point 62 in the edge. When the contrast image is formed in a position 64 at the other side at approximately the same distance from the reversing point 62, the difference in contrast medium concentration between the mask image and the contrast image will amount to from 20 to 40% of the maximum concentration. In the case of such a contrast concentration difference, usable difference images can be formed in dependence of the time difference between successive images. Motional unsharpness is now substantially precluded, because the time difference between mask image and contrast image now amounts to only from approximately 0.25 to 1 s. When mask images and contrast images have thus been formed, the process may be repeated in a next measuring position. It is not objectionable that the part of the object which is then situated in the image field already contains some contrast medium. The first mask image is again formed near the position 60, corresponding approximately to a concentration of one third of the peak concentration. The bolus can thus be followed through the object region to be examined. In the case of a customary flow rate of the contrast bolus, for example 4 images can be formed in each of the measurement positions, a sufficient amount of time remaining there between for displacement. It is to be noted that the position with respect to the bolus need not be exactly defined for the images. A given shift over the edge is simply permissible and results in no more than a smaller contrast medium difference and not in other image defects.

Reversing the time sequence between mask image and contrast image, a similar series of images can be formed at the rear 66 of the bolus. Thus, either a different indication can be given, for example, starting from the instant at which the concentration in the measuring field starts to decrease, passes the peak, or additional images can be obtained.

Via the method of injection, a difference in the shape of the bolus can also be achieved in order to simplify or improve given examinations.

Moreover, the contrast difference across the image field can be compensated for, if desirable, by means of leading edge images and trailing edge images. To this end, corresponding images from both edges can be added after which they are used as images to be subtracted. It will be apparent that this compensation can also be used for the previously described methods. When a plurality of images are formed on an edge, there is a free choice as to whether for the mask image use is always made of the first image of the ascending edge or the last image of the descending edge, or each time the last image but one. The use of the last image but one results in a smaller difference in contrast concentration but also in a smaller difference in the time, between exposures. Actually, the orginal difference between mask image and contrast image is substantially reduced according to the latter method.

In order to prevent image overradiation, a filter 52 is preferably used in the device. Even though a slight overradiation does not have serious effects due to the subsequent image subtraction, it should still be limited because overradiation may have a pronounced adverse effect on the optimizing of each of the sub-images, for example on their optimum exposure.

In a preferred embodiment of the invention, a lateral displacement of the object is achieved over 1.5 meters in from 5 to 10 steps.

What is claimed is:

1. A method of X-ray examination which comprises;
   propagating a bolus of contrast medium through an object undergoing examination;
   detecting a series of mask images and contrast images while the object contains different concentrations of said contrast medium and where each image is taken at a time when the contrast medium concentration is different from that of a previous image;
   subtracting a mask image from a corresponding adjacent contrast image taken when said object has a higher contrast medium concentration than said mask image; and
   laterally displacing the object with respect to an imaging system, the lateral displacement being coordinated with the propagation of the bolus through the object so that the mask images and the contrast images are both formed in rapid succession on the same edge of the bolus.

2. The method of claim 1 wherein the speed of said lateral displacement equals the speed of propagation of the bolus through the object.

3. The method of claim 1 wherein images are formed on both the leading edge and the trailing edge of the contrast bolus.

* * * * *